United States Patent [19]

Ægidius

[11] Patent Number: 5,258,285

[45] Date of Patent: Nov. 2, 1993

[54] METHOD FOR DETECTION OF BACTERIAL CONCENTRATION IN A SAMPLE

[75] Inventor: Poul E. Ægidius, Helsinge, Denmark

[73] Assignee: A/S Foss Electric Holding, Hillerod, Denmark

[21] Appl. No.: 196,690

[22] Filed: May 20, 1988

[30] Foreign Application Priority Data

May 21, 1987 [DK] Denmark .................... 2587/87

[51] Int. Cl.$^5$ .................................. C12Q 1/66
[52] U.S. Cl. .................................. 435/8; 435/4; 435/259; 435/291; 435/311; 436/807; 422/52; 422/81; 422/82; 422/82.05
[58] Field of Search ............ 435/8, 34, 39, 291, 435/259, 300, 311.4; 422/52, 81, 81, 82.05; 436/807

[56] References Cited

U.S. PATENT DOCUMENTS

| | | | |
|---|---|---|---|
| 3,616,253 | 10/1971 | D'Eustachio | 195/103.5 |
| 3,745,090 | 7/1973 | Chappelle et al. | 195/103.5 R |
| 3,971,703 | 7/1976 | Picciolo et al. | 195/103.5 R |
| 4,013,418 | 3/1977 | Plakas | 422/52 |
| 4,144,134 | 3/1979 | Plakas | 195/103.5 M |
| 4,283,490 | 8/1981 | Plakas | 435/8 |
| 4,303,752 | 12/1981 | Kolahmainan et al. | 435/34 |
| 4,385,113 | 5/1983 | Chappelle et al. | 435/8 |
| 4,421,848 | 12/1983 | Whitlock | 435/8 |

FOREIGN PATENT DOCUMENTS

| | | | |
|---|---|---|---|
| 0025351 | 3/1981 | European Pat. Off. | |
| 0101398 | 2/1984 | European Pat. Off. | |
| 0126019 | 11/1984 | European Pat. Off. | |
| 0161481 | 11/1985 | European Pat. Off. | 435/34 |
| 0238352 | 3/1987 | European Pat. Off. | |
| 8607094 | 12/1986 | PCT Int'l Appl. | 435/34 |
| 2059990 | 4/1981 | United Kingdom | |
| 2132633 | 7/1984 | United Kingdom | |

OTHER PUBLICATIONS

Darnall et al. *Molecular Cell Biology* Scientific American Books: New York (1986), pp. 167–169.
Jensen *Acta Pharmacol. Toxicol.* 38: 465–73, 1976.
Davies et al. *J. Appl. Bacteriol.* 31: 448–61, 1968.
Practical Immunology, Third Edition (1989) Hudson et al, p. 469 European Office Action of May 7, 1991.
Proceedings of Soc. for Experimental Biol. & Medicine, vol. 183, 1986, pp. 74–80, T. S. Tsai et al.
Rapid Methods & Automation in Microbiology; pp. 162–165, May 1981, H. H. Johnston et al.
International Symposium on Analytical Applns of Bioluminescence and Chemiluminescence, pp. 446–447, 1980, H. H. Johnston et al.

*Primary Examiner*—David Saunders
*Assistant Examiner*—Christopher L. Chin
*Attorney, Agent, or Firm*—Birch, Stewart, Kolasch & Birch

[57] ABSTRACT

The number of bacteria in a cell population comprising bacteria and somatic cells is determined by concentrating the bacteria and the somatic cells on the surface of a substrate of a filter material, such as a membrane filter, rupturing the somatic cells by treatment with a medium which is not in osmotic balance with the medium inside the cells, such as water which here constitutes a hypotonic medium, and removing or inactivating their ATP, establishing an extraction chamber having an inner wall which is partly defined by the bacteria-bearing surface of the filter material and therein extracting the ATP from the bacteria with a medium containing a surfactant, such as a quaternary ammonium compound, capable of perforating the cell walls of the bacteria, adding luciferin and luciferase and transferring the medium to a measuring chamber, determining the amount of ATP by measuring the light emitted as a result of the luciferin/-luciferase reaction and expressing the amount of ATP as the number of bacteria present on the substrate.

10 Claims, 1 Drawing Sheet

METHOD FOR DETECTION OF BACTERIAL CONCENTRATION IN A SAMPLE

FIELD OF THE INVENTION

The present invention relates to a method of detecting microbial cells in a sample. More particularly, the invention relates to a method for separating adenosine triphosphate (ATP) from somatic cells in a sample containing somatic cells and microbial cells. Furthermore, the invention relates to a method for determining the number of bacteria by bioluminescence or chemiluminescence assay.

BACKGROUND OF THE INVENTION

When determining the microbiological quality of biological materials, e.g. determining the number of bacteria in meat meant for human consumption, various attempts have been made to utilize bioluminescence reactions, in particular the so-called "firefly"-reaction or luciferin/luciferase reaction. In this reaction, adenosine triphosphate (ATP) reacts with luciferin in the presence of the enzyme luciferase while generating light, and this method is a rapid and sensitive method for determining ATP in a sample. Since ATP is present in practically all living cells, the method can be used for detecting the presence of somatic (eucaryotic), bacterial and fungal cells in a sample. When, as in the present case, the purpose particularly is to determine the number of bacteria, it becomes important to ensure that non-bacterial cells in the sample, in particular somatic cells (such as tissue cells from a meat sample) do not interfere with the measurement by contributing to the bioluminescence reaction with their own ATP. In other words, it becomes important to ensure that only ATP from bacterial cells is subjected to the bioluminescence reaction whereas it should be prevented that ATP from somatic cells takes part in the reaction.

One way of achieving this would be to selectively lyze the somatic cells without disturbing the microbial cells, but methods used so far invariably describe the use of some kind of active lyzing agent which commonly is some kind of surfactant. Thus, U.S. Pat. No. 4,303,752 describes the selective removal of ATP from somatic cells in a mixture of somatic and microbial cells by treating the sample with a non-ionic surfactant, e.g. an ethoxylated alkyl phenol. However, it is also known that a number of non-ionic surfactants can cause inhibition of the luciferase enzyme in the subsequent bioluminescence assay which means that any remains of non-ionic surfactant that has not been removed will significantly reduce the light output and consequently reduce the sensitivity of the assay.

With respect to the subsequent bioluminescence assay, previous commercially available methods for carrying out this assay have employed glass containers (cuvettes), in which both rupture of the somatic cells, inactivation of the released somatic ATP, release of bacterial ATP, and reaction with luciferin/luciferase takes place in the same container. Such a system has a number of drawbacks. Firstly, since the somatic ATP cannot be removed physically from the medium, it is necessary to use an enzyme (somase) to render the somatic ATP inactive, which in turn necessitates the subsequent inactivation of the enzyme prior to the release of the bacterial ATP. Secondly, the presense of cell fragments and remains in the medium reduces the sensitivity of the luminescent reaction because of scattering of the light emitted during the reaction. Consequently, this method is not well suited to determining the low concentrations of bacteria encountered within the food quality control field, quite apart from the extra several inactivation steps necessary.

Other suggested methods which, however, have not resulted in commercially available instruments, have employed having the now purified bacterial material present on the surface of a substrate such as a filter surface and lowering a container part onto the substrate to form a closed measuring chamber, the container part comprising means for detecting light such as a photomultiplier. However, the fact that one of the walls of the measuring chamber is formed by the filter surface, on which the bacteria to be counted are situated, makes it difficult to ensure that the measuring chamber is completely light-proof; the porous and/or translucent quality of most filtering materials will cause difficulties when attempting to provide a completely light-proof seal between the container part and the surface of the filter material.

SUMMARY OF THE INVENTION

The present invention firstly concerns a method for substantially selectively removing adenosine triphosphate (ATP) from somatic cells in a sample containing somatic cells and bacteria which method comprises treating the sample with water to rupture the membranes of the somatic cells and substantially removing or inactivating the ATP released.

The ability of water to function as the sole treatment material for causing the somatic cells to release their ATP is due to the fact that the somatic cells, unlike the majority of bacteria, are not surrounded by a cell wall as the outermost boundery, but only by a fragile cell membrane. Therefore, treating the somatic cells with a medium which is not in osmotic balance with the medium inside the cells, in the case of water a hypotonic medium, will cause the cells to swell and rupture thereby releasing their content of ATP. In view of the intent effort by previous workers to cause selective removal of somatic ATP only by the use of various treatment agents, it is surprising that a simple treatment with water is able to substantially selectively remove the ATP from the somatic cells in the sample.

It is advantageous that the somatic cells in the sample are present as single cells or very small cell aggregates since this will further enhance the osmolytic effect of the water treatment. For example, the sample containing somatic cells and bacteria may be obtained from a meat sample, the microbial quality of which is to be determined. As an example of the pre-treatment of the sample, a measured amount of meat may be mixed with a measured amount of a pre-treatment liquid or diluent (such as physiological saline, optionally containing peptone) and treated mechanically, e.g. by kneading followed by separation of the liquid part of the sample and separating larger cell aggregates from the obtained liquid by e.g. filtration or centrifugation. The sample (without the larger cell aggregates) will then comprise on the one hand bacteria released from the sample and on the other hand single somatic cells or small aggregates of somatic cells. The diluent assists in preparing the somatic cells for the subsequent water treatment in that the diluent "degreases", that is removes fat, from the surface of the somatic cells. The diluent may further contain a buffer such as a citrate/phosphate buffer at a pH around 5.5.

In a preferred embodiment the treatment of the sample with water is carried out in a layer of water above the surface of a substrate material, the substrate preferably being a filter material, in particular a membrane filter. In order to accelerate the release of somatic ATP, the water phase may further be subjected to agitation or stirring in order for the mechanical stress thus applied to aid in rupturing the cells. Also, thermal stress may be applied by heating the water phase to a temperature in the range of 35°-45° C. Finally, the filtering process also applies a mechanical stress on the somatic cells, thus further facilitating the rupture of the cells.

To remove the released somatic ATP, the bacteria and cell fragments may be separated from the water phase and may be washed with a further amount of water. In case of the treatment with water being carried out above the surface of a filter material, the separation of the somatic cell remains and the whole bacteria from the water phase may usefully be carried out by filtration followed by, as described above, washing with a further amount of water to ensure complete removal of the released somatic ATP.

The present invention further concerns a method for determining the number of bacteria on the surface of the substrate, said method comprising a) forming a closed chamber having an inner wall which is partly defined by the bacteria-bearing surface of the substrate;
b) contacting the bacteria-bearing surface with an aqueous extraction medium capable of perforating the cell walls of the bacteria and extracting substantially all of the ATP present in the bacteria;
c) transferring the extraction medium to a separate measuring chamber;
d) adding luciferin and luciferase to the extraction medium so as to subject the ATP in the extraction medium to a luciferin/luciferase reaction; and
e) determining the amount of ATP by measuring in the measuring chamber the light emitted as a result of the reaction and expressing the amount of ATP as the number of bacteria present on the substrate.

The advantage of the above method is that the extraction of the ATP from the bacteria and the measurement of the light emitted during the luciferin/luciferase reaction takes place in two separate chambers thereby eliminating the above-mentioned problems associated with carrying out the extraction and the light emission measurement in the same chamber. By moving the light measurement into a separate measuring chamber, it becomes possible on the one hand to avoid the entry of false light due to an incomplete light-proof junction between the substrate surface and the chamber of which the substrate forms one of the walls and on the other hand to enhance the photon efficiency of the light measurement, e.g. by providing the measuring chamber with reflecting walls.

It will be obvious to the person skilled in the art that the above steps a)–e) need not necessarily be carried out in the listed order. Thus, the addition of luciferin and luciferase to the extraction medium in step d) may just as well be carried out simultaneously with the extraction reaction in step b) or immediately prior to or simultaneously with the transfer of the extraction medium in step c).

Since it is preferred that the transfer in step c) of the extraction medium from the closed chamber to the measuring chamber is carried out by pumping, it will be clear that step d) may be carried out by adding luciferin and luciferase to the extraction chamber during the extraction reaction in step b) or immediately prior to the transfer of the extraction medium to the measuring chamber; during the transfer of the extraction medium from the closed chamber to the measuring chamber (e.g. through a T-connection); as well as adding the luciferin and luciferase to the extraction medium after it has been transferred to the separate measuring chamber. In other words, although some constraints are placed on the order of steps a)–e) [e.g. that step a) would almost invariably be carried out first and step e) last], the skilled art worker has considerable latitude with respect to the exact order of the extraction, transfer and luciferin/-luciferase-addition operations, and the method of the invention consequently encompasses within its scope any sequential combination of the steps a)–e) above.

The use of two separate chambers, namely an extraction chamber and a measurement chamber, also makes it possible to ensure good homogeneity of the media during both the extraction operation and the measurement operation.

In a preferred embodiment, the homogeneity during the extraction operation in step b) may be ensured by repeatedly pumping the extraction medium out of the extraction chamber and back again in order to distribute the released ATP homogeneously in the extraction medium. In order to avoid the necessity of a third reservoir, the extraction medium may suitably be pumped from the extraction chamber to the measuring chamber and back in order to achieve the homogeneity.

Also, homogeneity of the medium after the addition of lucifarin and luciferase in step d) may be ensured by, prior to step e), repeatedly pumping the extraction medium away from the measuring chamber and back in order to distribute the added luciferin and luciferase homogeneously in the medium, thereby providing the possiblity of a maximum exploitation of the luminescent components and the best possible photon efficiency.

It is preferred that the aqueous extraction medium contains one or more cationic surfactants, in particular selected from quarternary ammonium compounds such as N-cetyl-N,N,N-trimethylammonium bromide, dodecyltrimethylammonium bromide, diemthyldioctadecylammonium bromide, didodecyldimethylammonium bromide, benzyltriethylammonium chloride, benzyldimethylhexadecylammonium chloride, tetradecyltrimethylammonium bromide, ethylhexadecyldimethylammonium bromide, dodecyltrimethylammonium chloride, benzalkonium chloride, and mixtures thereof. The extraction medium may further contain chlorhexidine digluconate, chlorhexidine acetate or 2-phenylethanol.

The substrate on which the bacteria are situated initially is preferably a filter material, in particular a membrane filter. Thus, the substrate may, preferably, be identical to the filter material used in the above-described method for substantially selectively removing ATP from somatic cells in a sample containing somatic cells and bacteria.

BRIEF DESCRIPTION OF THE DRAWING

The drawing schematically shows a preferred embodiment of an apparatus for performing the method of the invention.

In the following, an apparatus performing the method of the invention in preferred embodiments will be explained in detail by reference to FIG. 1.

Figure 1:
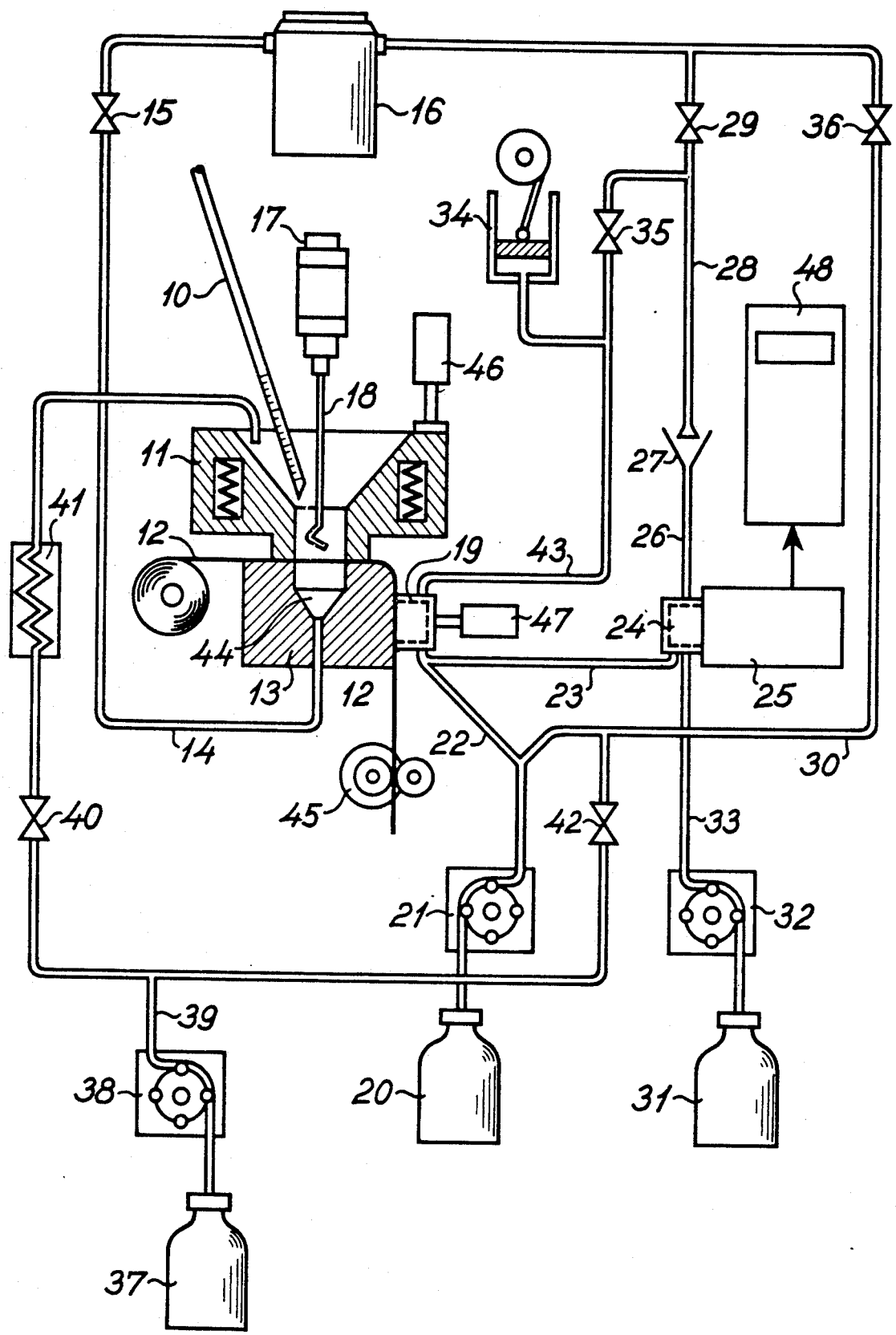

Through a sample feed line 10, a liquid sample containing bacteria and somatic cells is dispensed into a thermostated funnel 11. The sample may be diluted with a diluent which may also serve to transfer all bacteria present in the sample feed line 10 into the funnel 11. The funnel 11 rests on a filter block 13 with a filter paper strip 12 present between the funnel 11 and the filter block 13. The filter block 13 contains a cavity 44 which is aligned with the lower opening of the funnel 11 and is also connected to a vacuum line 14 leading to a vacuum tank 16 via a valve 15. By applying vacuum to the cavity 44, the sample present in the funnel 11 is filtered through the filter strip 12 leaving the bacteria and the somatic cells on the surface of the filter strip. In order to remove ATP from the somatic cells in the sample, the sample consisting of bacteria and somatic cells is then, according to the invention, treated with water. The water is dispensed from a water container 37 by means of a peristaltic pump 38 through a water feed line 39 and regulated by a valve 40. In order to subject the somatic cells to thermal stress, the water is thermostated in a thermostating coil 41 before being dispensed into the funnel 11. The water containing the bacteria and the somatic cells in the funnel 11 is also stirred by means of a stirrer 18 powered by a motor 17 and in order to subject the somatic cells to mechanical stress as well. As a result of the treatment with water, the thermal stress and the mechanical stress, the membrane of the somatic cells ruptures and the somatic cells empty their content of ATP into the water medium. The water is then removed by filtering through the filter strip 12 by employing vacuum to the cavity 44. The water treatment process may be repeated several times.

By means of retraction means 46, the funnel 11 is lifted from the filter strip 12, and the filter strip 12 is by means of a traction motor 45 hold around the edge of the filter block 13 to position underneath an open chamber 19 which then, by means of closing means 47 is lowered onto the part of the surface of the filter strip comprising the bacteria and the ruptured somatic cells to form an enclosed chamber. The chamber 19 is connected to a line 43 and lines 22 and 23, lines 22 and 23 joining oneanother at the point at which they are connected to the chamber 19. From a tank 20, an aqueous extraction medium is pumped by means of a peristaltic pump 21 through the line 22 and into the line 23 (but not into the chamber 19 which is filled with air), into and through a measuring chamber 24, through a line 26 and into a funnel 27. In the funnel 27, excess extraction medium is sucked off by means of a vacuum line 28 connected to the vacuum tank 16 via a valve 29. In this manner, a fixed volume of extraction medium is dispensed into the system, the volume being defined by the total volume of the line 23, the measuring chamber 24, the line 26 and the funnel 27 up to the level at which the opening of the vacuum line 28 is positioned within the funnel 27.

Line 43, which is filled with air, connects the chamber 19 with a reciprocating pump 34 which is also connected to the vacuum circuit via a valve 35. Following the dispensation of the correct amount of aqueous extraction medium into the system, the pump 34 is operated to pump the extraction medium from line 26 and the measuring chamber 24 into the chamber 19 where it is brought into contact with the bacteria present on the surface of the filter strip 12. The extraction medium will perforate the cell wall to the bacteria and extract substantially all of the ATP present in the bacteria. In order to ensure a homogeneous distribution of the extracted ATP in the aqueous extraction medium, the pump 34 is operated in a reciprocating manner to pump the aqueous extraction medium into the chamber 19, out of the chamber 19 and into the measuring chamber 24 several times, the pump being stopped when a majority of the extraction medium is present in the measuring chamber 24. During the reciprocating transfer of the extraction medium, now containing the ATP extracted from the bacteria, a measured amount of luminescence reagent containing luciferin and luciferase is dispensed from a tank 31 by means of a peristaltic pump 32 through a line 33 into the measuring chamber 24. In a preferred embodiment, the reciprocating transfer of the extraction medium between the chamber 19 and the measuring chamber 24 is continued for a short time after the dispensation of the luminescent reagent in order to distribute this homogeneously in the entire volume of extraction medium. When the pump 34 is stopped, the extraction medium, now containing bacterial ATP as well as luciferin and luciferase, is present in the measuring chamber 24, where the light generated by the luminescent reaction between luciferin, luciferase and ATP is measured by means of the photomultiplier 25. The photomultiplier 25 is connected to a counter system 48 counting the number of pulses emitted by the photomultiplier as a result of the luminescent reaction.

As a last operation, the system is emptied and cleaned to prepare for the next sample. For cleaning purposes, water from the tank 37 or the diluent mentioned above used for cleaning the pipette may be dispensed through a valve 42 into the line 30 and may be transferred through the system by applying vacuum to the system either through the valve 35 or a valve 36, the system consisting of lines 22, 23, 26 and 43, the chamber 19, the measuring chamber 24 and the pump 34 ending up by being empty of liquid and dry. In this manner, the system is prepared for a new measuring cycle.

Since the luciferin/luciferase/ATP-reaction has its maximum reaction efficiency at around 22° C., it is preferred that the line 23 connecting the extraction chamber and the measuring chamber 24 also comprises means for accurately thermostating the medium flowing through the line 23, the thermostating means particularly being of a type capable of both heating and cooling the medium such as a Peltier element.

In order to improve the thermostating conditions in line 23, it is preferred that line 23 has a relatively high length/diameter ratio such as from 50 to 300, preferably from 100 to 200, such as around 150.

Another aspect of the invention is a sample diluent, the purpose of which is to ensure complete transfer of all bacteria present in a sample-containing device such as the sample feed line 10 on the drawing into a sample receptacle such as the funnel 11. It is preferred that the sample diluent has a pH of 4-8, in particular 5-7, especially around 5.7. The diluent may comprise a citrate/phosphate buffer, in particular containing citric acid and $Na_2HPO_4$ or a hydrate thereof, in particular $Na_2HPO_4.2H_2O$. The amounts of the buffer components may be e.g. from 6.45 to 0.29 g/l citric acid, in particular 5.1-1.8, especially around 4.55 g/l citric acid, as well as 6.9-17.3 g/l $Na_2HPO_4.2H_2O$, in particular 9.0-14.6 g/l, especially around 10.56 g/l $Na_2HPO_4.2H_2O$. In samples containing significant amounts of fat (e.g. milk samples), the diluent may also contain small amounts of a surface active agent in order to facilitate filtration of the sample by aiding the fat globules of the fat-containing sample to pass through the filter material. The surfactant may be selected from a large variety of such materials but is preferably a non-ionic detergent such as e.g. Triton ® X-100 (polyethylene glycol p-isooctylphenyl ether, from Rohm & Haas, West Germany), the surfactant being present in amounts of up to 0.01%. However, the presence of the surfactant in fat-containing samples is optional since it has been found that reliable results may be obtained even without the use of surfactant.

Yet another aspect of the invention is an extraction medium for use in extracting the ATP present in the bacteria. As described above, this extraction is performed subsequent to removal of ATP from somatic cells. The extraction medium preferably contains a cationic surfactant, in particular a quarternary ammonium surfactant selected from those mentioned above such as N-cetyl-N,N,N-trimethylammonium bromide (CTAB) as well as chlorhexidine digluconate. Due to the particular manner in which the luminescent reaction is performed, namely in a separate chamber, it is important to adapt the composition of the extraction medium to the time profile of the reaction. Thus, a luciferin/luciferase reaction can be carried out to emit the light as a fairly short pulse or as a longer-lasting emission depending on the properties of the extraction medium with respect to accelerating/retarding the light emitting reaction. This is in part due to the fact that the product released during the reaction, namely oxyluciferin, exerts an inhibiting activity on the enzyme luciferase. Thus, only a very small amount of the ATP present in the sample actually enters into the reaction to release light before the enzyme is inhibited or the reaction must be terminated for time reasons. Consequently, it is instead the property that the light emission intensity is proportional to the concentration of ATP which is exploited. In the present case, the actual light measurement is conducted a few seconds after the admixture of luciferin/luciferase to the extracted sample, and an extraction medium useful in the method of the invention should therefore be adapted in such a way that the maximum light emission takes place when the sample has reached the measurement chamber.

Therefore, in a preferred embodiment, the extraction medium contains 0.02-1.0 g/l CTAB and 0.1-16.0 g/l chlorhexidine digluconate, especially 0.1 g/l CTAB and 0.5 g/l chlorhexidine digluconate.

The invention is further illustrated by means of the following examples.

EXAMPLE 1

The experiments were carried out in an apparatus of the type illustrated on the drawing in which the extraction chamber was cylindrical with a diameter of 10 mm and a depth of 1 mm, the measuring chamber was also cylindrical with a diameter of 10 mm and a depth of 1 mm, and the tube (line 23) connecting the two chambers had a length of 70 mm and an internal diameter of 0.5 mm. The pump 34 was a piston pump with a displacement volume of 100 µl. The diluent used for flushing the pipette 10 was a citrate/phosphate buffer containing 4.55 g/l citric acid and 10.56 g/l $Na_2HPO_4.2H_2O$ having a pH of ca. 5.7. The extraction medium was a solution of 0.1 g/l N-cetyl-N,N,N-trimethylammonium bromide and 0.50 g/l chlorhexidine digluconate.

The luciferin/luciferase reagent was prepared from a commercially available reagent from Lumac/3M, the Netherlands. The commercially available package consists of a freeze dried preparation containing D-luciferin, purified firefly luciferase, bovine serum albumin, and dithiothreitol and was prepared in a special buffer from the same company containing 0.025M Hepes (N-2-hydroxyethylpiperazine-N'-2-ethane sulphonic acid) 0.0075M magnesium sulphate, 0.001M EDTA and 0.02% sodium azide.

100 µl of a sample was by means of the pipette 10 introduced into the funnel 11 and washed with $3 \times 1.3$ ml diluent with stirring after which the sample was treated with 1.3 ml water at 37° C. while stirring. The filter was then transported to the position under the open chamber 19 which was then fitted on top of the filter after which 500 µl extraction medium were pumped through lines 22 and 23 (but not into the chamber 19), through the measuring chamber 24 and into the funnel 27 where the surplus was removed by vacuum leaving a volume of 120 µl extraction medium in the system. By means of the pump 34, the extraction medium was pumped into the extraction chamber and out again a total of 15 times.

During one of the active pump strokes, 20 µl luciferin/luciferase reagent was added through line 33 after which the pump 34 concluded a further two pump cycles between the extraction chamber and the measuring chamber 24 leaving the liquid in the measuring chamber for detection by means of the photomultiplier, the signal from which was quantified electronically in a standard manner.

Ten samples of raw ground beef were analysed, the samples containing from $3 \times 10^4$ to $10^8$ bacteria per gram determined by the standard plate counting method. For analysis, 10 g sample was put in a sterile plastic bag, mixed with 90 g of a 0.9% saline solution containing peptone and kneaded for 30 seconds in a so-called "Stomacher". Ca. 7 ml of the homogenised sample was centrifuged at 1000 rpm for 30 seconds, and the supernatant was analysed in the apparatus in the above described manner. Each meat sample was prepared and analysed 3 times.

The results were compared statistically with the plate count results by linear regression analysis which showed a standard deviation around the regression line of 7% relative, which is better than the normally attainable repeatability with the plate count method. The contribution from somatic ATP was constant and could be removed by calibration without affecting the standard deviation of the accuracy.

EXAMPLE 2

In the present example, the same instrument employed in Example 1 was used for measurement on samples of raw milk. All samples were raw milk from incoming tankers, and the milk was pre-heated to 40° C. and mixed gently (by inversion) before presentation to the instrument. Result comparison was made against total viable count (TVC) determined by the spiral plating technique on Bacto Plate Count Agar (Difo) incubated at 21° C. for four days. The necessary dilutions were made in aqueous NaCl-peptone solution (8.5 g NaCl and 1.0 g peptone in 1 liter distilled water).

The various diluents and reagents were identical to those employed in Example 1 with the exception of the diluent used for rinsing the pipette (i.e. during the initial filtration phase), where 0.01% by weight of Triton ®

X-100 was added to the diluent in order to facilitate filtration by aiding the fat globules in the milk to pass through the filter material. However, the addition of the non-ionic detergent Triton ® X-100 is not at all vital; experiments conducted without the addition of Triton ® X-100 gave excellent results, the only difference being that the repeatability of the results was slightly better in the case in which Triton ® X-100 had been added. There was no significant difference between the mean values of the results.

RESULTS

In a first group of experiments, measurements were made on 185 samples of raw milk from individual tankers at a Danish dairy, and comparisons were made between total light count and total viable count. In order to expand the dynamic range from $10^4$–$10^6$ to $10^4$–$10^8$ CFU/ml, ten of the samples were stored for 24 hours at 6° C. before analysis. Linear regression between log (light count) and log (TVC) yielded a correlation coefficient of 0.92, a slope of the regression line of 1.17 and a standard deviation of estimate of 0.28 log cycle.

In a second group of experiments, measurements were performed at a West German dairy in order to investigate how variations and the composition of the milk and the flora would affect the result. 119 individual samples of raw milk from incoming tankers were analysed in the same manner as the first group of experiments. The regression of log (light count) versus log (TVC) showed a regression line with a slope of 0.95, a correlation coefficient of 0.88 and a standard deviation of estimate of 0.21 log cycle.

Based on the two groups of results above, a joint statistical analysis of all the data on all 304 samples was conducted to assess the performance of the instrument on bulk milk. The analysis showed a correlation coefficient of 0.92, a slope of 1.17 and a standard deviation of estimate of 0.27 log cycle.

DISCUSSION

In this experiment, all results from the instrument were presented in arbitrary light units without any sort of calibration conducted in the instrument. The instrument delivered the results expressed as CFU/g.

The ten highest contaminated samples in the first group of experiments were, as indicated, incubated for 24 hours at 6° C. These samples were included in order to expand the contamination levels to extend over four decades and to verify the performance and dynamic range of the method of the invention. The linear relationship between luminescence and TVC on bulk milk down to $10^4$ CFU/ml, a regression line with a slope close to 1 and a small standard deviation of estimate mean that there is no residual somatic ATP on the filter when the microbial ATP is extracted, thereby verifying the efficiency of the somatic ATP extraction step. Previous investigations on milk have shown difficulties in removing somatic ATP and were consequently unable to detect contamination levels below $10^5$ CFU/ml (Bossuyt, R. "Determination of Bacteriological Quality of Raw Milk by an ATP Assay Technique", *Milchwissenschaft* 36(5), 1981, p. 257-260; Theron, D. P., Prior, B. A. and Latagan, P. M. "Determination of Bacterial ATP Levels in Raw Milk: Selectivity of Non-bacterial ATP Hydrolysis", *Journal of Food Protection* 49(1), 1986, p. 4–7). A slope close to 1 means that the luminescence signal is directly related to TVC. This simple relationship has been verified many times in growth curve studies involving ATP measurements and conventional TVC determinations illustrating that ATP levels increase parallelly with TVC during the logarithmic growth phase.

I claim:

1. A method for determining the number of bacteria in a cell population comprising bacteria and somatic cells, comprising
    a) providing an apparatus with means for filtering and concentrating said cell population, an extraction chamber, and a measuring chamber, said means for filtering and concentrating said cell population comprising a sample receiving means with a movable filter material, said means for filtering and concentrating connected to said extraction chamber by said filter material and said extraction chamber being connected with the measuring chamber by means of a line, the measuring chamber being provided with light detecting means capable of detecting light emitted from a sample as a result of a bioluminescence reaction in the measuring chamber with ATP from the bacteria;
    b) filtering a sample containing bacteria and somatic cells on said filter material and thereby concentrating the cells on a surface of said filter material;
    c) rupturing the membranes of the somatic cells in said filter material, and substantially removing ATP released from the ruptured somatic cells through the filter material;
    d) moving the filter material which contains the concentrated bacteria cells to the extraction chamber;
    e) contracting the bacteria-bearing surface of the filter material with a predetermined volume of an aqueous extraction medium capable of perforating the cell walls of the bacteria and extracting ATP from the perforated bacteria cells into the extraction medium, wherein the extraction medium is repeatedly pumped into and out of the extraction chamber by a pumping means which is connected to the extraction chamber by an air-filled line; and
    f) transferring the extraction medium to the measuring chamber and establishing, in the measuring chamber, a bioluminescence reaction with the bacterial ATP, determining the amount of ATP by measuring, by means of the light detecting means, the light emitted as a result of the bioluminescence reaction, and expressing the amount of ATP as the number of bacteria present on the filter material.

2. The method according to claim 1, wherein the bioluminiscence reaction is established by adding luciferin and luciferase to the ATP-containing extraction medium.

3. The method according to claim 2, in which the luciferin and luciferase are added while the extraction medium is repeatedly pumped into and out of the extraction chamber by the pumping means connected to the extraction chamber through the air-filled line in order to distribute the luciferin and luciferase homogeneously in the medium.

4. The method according to claim 1, in which the aqueous extraction medium contains one or more cationic surfactants.

5. The method according to claim 4, in which the cationic surfactant is selected from the group consisting of N-cetyl-N,N,N-trimethylammonium bromide, dodecyltrimethylammonium bromide, dimethyldioctadecylammonium bromide, didodecyldimethylammonium bromide, benzyltriethylammonium chloride, benzyldimethyl-hexadecylammonium bromide, tetradecyltrimethylammonium bromide, ethylhexadecyldimethylammonium bromide, benzalkonium chloride, and mixtures thereof.

6. The method according to claim 1, in which the movable filter material is a membrane filter material.

7. The method according to claim 1, wherein the extraction medium used in step (e) contains from 0.02 to 1.0 g/l N-cetyl-N,N,N-trimethylammonium bromide (CTAB) and from 0.1 to 16.0 g/l chlorohexidine digluconate.

8. The method according to claim 1, wherein a diluent containing from 6.45 to 0.29 g/l citric acid and from 6.9 to 17.3 g/l $Na_2HPO_4.2H_2O$, with pH in the range from 4 to 8 is added to the sample being filtered.

9. The method according to claim 8, wherein the diluent contains from 5.1 to 1.8 g/l citric acid and from 9.0 to 14.6 g/l $Na_2HPO_4.2H_2O$, the diluent having pH in the range from 5 to 7.

10. The method according to claim 1 in which the rupturing of the somatic cells is performed by treatment of the cell population with water, and the removal of the released ATP from the ruptured somatic cells through the filter material is carried out by washing with water.

* * * * *

UNITED STATES PATENT AND TRADEMARK OFFICE
CERTIFICATE OF CORRECTION

Page 1 of 2

PATENT NO. : 5,258,285
DATED : November 2, 1993
INVENTOR(S) : Ægidius

It is certified that error appears in the above-indentified patent and that said Letters Patent is hereby corrected as shown below:

Claim 1, col. 10, line 32, change "contracting" to --contacting--

Claim 8, col. 12, line 1, change "$Na_2HPO_4.2H_2O$" to --$Na_2HPO_4 \cdot 2H_2O$--

Claim 9, col. 12, line 5, change "$Na_2HPO_4.2H_2O$" to --$Na_2HPO_4 \cdot 2H_2O$--

Col. 3, line 12, change "° C" to --°C--

Col. 4, line 36, change "lucifarin" to --luciferin--

Col. 6, line 43, change "° C" to --°C--
    lines 62-63, change "$Na_2HPO_4.2H_2O$" to --$Na_2HPO_4 \cdot 2H_2O$--
    line 66, change "$Na_2HPO_4.2H_2O$" to --$Na_2HPO_4 \cdot 2H_2O$--
    line 67, change "$Na_2HPO_4.2H_2O$" to --$Na_2HPO_4 \cdot 2H_2O$--

Col. 7, line 65, change "$Na_2HPO_4.2H_2O$" to --$Na_2HPO_4 \cdot 2H_2O$--

Col. 8, line 14, change "° C" to --°C--
    line 57, change "° C" to --°C--
    line 62, change "° C" to --°C--

UNITED STATES PATENT AND TRADEMARK OFFICE
CERTIFICATE OF CORRECTION

PATENT NO. : 5,258,285
DATED : November 2, 1993
INVENTOR(S) : Aegidius

It is certified that error appears in the above-indentified patent and that said Letters Patent is hereby corrected as shown below:

Col. 9, line 19, change "° C" to --°C--
line 47, change "° C" to --°C--.

Signed and Sealed this

Thirtieth Day of August, 1994

Attest:

BRUCE LEHMAN

Attesting Officer

Commissioner of Patents and Trademarks